United States Patent [19]

Kurahashi et al.

[11] Patent Number: 4,729,998
[45] Date of Patent: Mar. 8, 1988

[54] CYCLIC CARBAMATES AND FUNGICIDAL USE

[75] Inventors: Yoshio Kurahashi, Tokyo; Shinzo Kagabu, Gifu; Noboru Matsumoto, Tokyo; Takayo Yamada, Tokyo; Katsuaki Wada, Tokyo, all of Japan

[73] Assignee: Nihon Tokushu Noyaku Seizo K.K., Tokyo, Japan

[21] Appl. No.: 31,349

[22] Filed: Mar. 26, 1987

[30] Foreign Application Priority Data

Apr. 4, 1986 [JP] Japan .................................. 61-76625

[51] Int. Cl.⁴ .................. A01N 43/86; C07D 491/06; C07D 498/06
[52] U.S. Cl. ..................... 514/226; 514/228; 514/234; 514/239; 544/32; 544/89; 546/166; 548/491
[58] Field of Search ................ 544/32, 89; 514/226, 514/228, 234, 239

[56] References Cited

FOREIGN PATENT DOCUMENTS 0103797 9/1983 European Pat. Off. .
62829 6/1978 Japan .
132232 10/1979 Japan .
2080296 2/1982 United Kingdom .

OTHER PUBLICATIONS

Agent for controlling Plant Disease, Nov. 29, 1980, vol. 4, No. 173 (C-32) (655), Cl.

*Primary Examiner*—Richard L. Raymond
*Attorney, Agent, or Firm*—Sprung Horn Kramer & Woods

[57] ABSTRACT

Fungicidally active cyclic carbamates of the formula

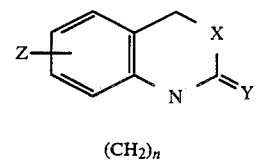

in which
  X and Y each represent oxygen or sulfur,
  Z represents hydrogen, halogen, alkyl or nitro, and
  n is 2 or 3.

Some intermediates are new.

10 Claims, No Drawings

CYCLIC CARBAMATES AND FUNGICIDAL USE

The present invention relates to novel cyclic carbamates, to several process for their preparation and to their use as agricultural fungicides.

It has already been disclosed that certain benzoxazine derivatives have agricultural fungicidal activities (see Japanese Laid-open Pat. No. 62,829/1978) and that certain benzazole derivatives also have agricultural fungicidal activities, (see Japanese Laid-open Pat. No. 132232/1979).

Novel cyclic carbamates of the formula (I)

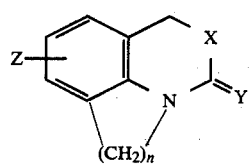

in which
X and Y each represent oxygen or sulfur,
Z represents hydrogen, halogen, alkyl or nitro, and
n is 2 or 3,
have been found.

Cyclic carbamates of the formula (I) are obtained by a process in which (a) in the case where X and Y each represent oxygen and Z represents hydrogen, halogen or alkyl, a compound of the formula (II)

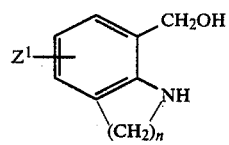

wherein
n has the meaning mentioned above, and
$Z^1$ represents hydrogen, halogen or alkyl,
is reacted with trichloromethyl chloroformate in the presence of an inert solvent, or (b) in the case where X and Y each represent sulfur and Z has the same meaning as those of $Z^1$, a compound of the formula (II) is reacted with carbon disulfide, in the presence of inert solvents, if appropriate, in the presence of alkali metal hydroxide, or (c) in the case where X represents sulfur, Y represents oxygen and Z has the same meanings as those of $Z^1$, a compound of the formula (II) is reacted with carbonyl sulfide, in the presence of inert solvents, if appropriate, in the presence of alkali metal hydroxide, or (d) in the case where X and Y each represent oxygen and Z represents nitro.
a compound of the formula (III)

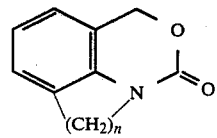

wherein
n has the meaning mentioned above, is reacted with nitric acid, in the presence of inert solvents.

The novel cyclic carbamates exhibit powerful agricultural fungicidal properties.

Suprisingly, the cyclic carbamates according to the invention exhibit a substantially greater fungicidal action in the agricultural field then those known from the aforesaid prior art and specifically as shown in biological tests hereinafter, the cyclic carbamates of the invention have, for example, excellent fungicidal activities against rice blast (*Pyricularia oryzae*).

Among the cyclic carbamates according to the invention, of the formula (I), preferred compounds are those in which
X and Y each represent oxygen,
Z represents hydrogen, fluorine, chlorine, bromine, nitro or alkyl with 1 to 4 carbon atoms, and
n is 2 or 3.

Very particularly preferred cyclic carbamates of the formula (I) are those in which
X and Y each represent oxygen,
Z represents hydrogen, fluorine, chlorine, bromine, methyl or ethyl, and
n is 2.

Specifically, the following compounds may be mentioned:
4,5-dimethylene-2,4-benzoxazin-3-one,
7-chloro-4,5-dimethylene-2,4-benzoxazin-3-one.

If for instance, 7-hydroxymethyl-2,3-dihydroindole and trichloromethyl chloroformate are used as starting material in the process (a) for the preparation of the compounds according to the invention, the course of the reaction may be represented by the following equation:

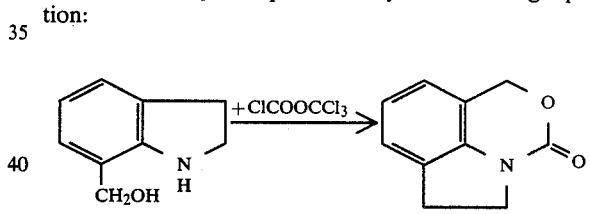

Likely, if 8-hydroxymethyl-1,2,3,4-tetrahydroquinoline and carbon disulfide are used as starting materials in the process (b), the course of the reaction may be represented by the equation:

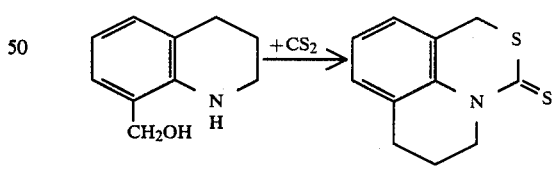

If 8-hydroxymethyl-1,2,3,4-tetrahydroquinoline and carbonyl sulfide are used as starting material in the process (c), the course of the reaction may be represented by the equation:

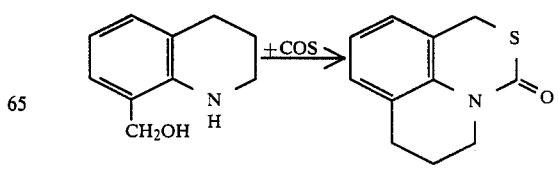

If 4,5-dimethylene-2,4-benzoxazine-3-one and nitric acid are used as starting materials in the process (d), the course of the reaction may be represented by the equation:

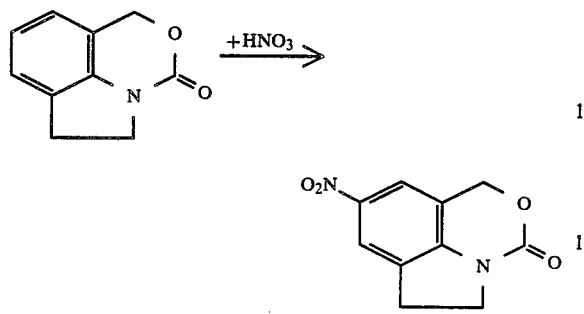

In the process (a), (b) and (c), the compounds of the formula (II) have the meanings, based on the definitions of $Z^1$ and n. In formula (II), $Z^1$ and n preferably have the meanings already given above.

The compounds of the formula (II) include certain novel compounds. Examples of the novel compounds of the formula (II) are as follows:

7-hydroxymethyl-2,3-dihydroindole;
8-hydroxymethyl-1,2,3,4-tetrahydroquinoline and
5-chloro-7-hydroxymethyl-2,3-dihydroindole.

The above-mentioned 8-hydroxymethyl-1,2,3,4-tetrahydroquinoline may be produced according to a method, which is described in J. Chem. Soc. Perkin Translation, Vol. 2, No. 12, p. 1778 (1980). The compounds of the formula (II) can generally be prepared according to a process wherein a compound of the formula (IV)

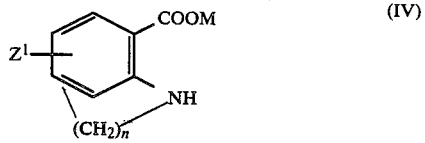

wherein $Z^1$ and n have the meanings mentioned above, and M represents hydrogen or lower alkyl, is reduced with lithium aluminum hydride or the like.

The compounds of the formula (IV) include known compounds, an example of which is 1,2,3,4-tetrahydroquinoline-3-carboxylic acid, as disclosed in J. Chem. Soc., Vol. 68, p. 1844 (1946). The compounds (IV) may generally be produced in a conventional manner by reducing a known quinoline-8-carboxylic acid (J. Chem. Soc., Vol. 68, p. 1844 (1946)), or reducing an indole-7-carboxylic acid methyl ester (Japanese Patent Application Disclosure No. 14511-1976) or a derivative thereof.

The compounds of the formula (III), which are employed as starting material in the process (d), may be prepared according to the process (a) and they are compounds according to the invention.

The process (a) is preferably carried out in the presence of a suitable solvent or diluent. Virtually all inert organic solvents can be used for this purpose.

Example of such solvents are aliphatic, cycloaliphatic and aromatic, optionally chlorinated, hydrocarbons, such as hexane, cyclohexane, petroleum ether, ligroin, benzene, toluene, xylene, methylene chloride, chloroform, carbon tetrachloride, ethylene chloride, trichloroethylene and chlorobenzene; ethers, for example, diethyl ether, methyl ethyl ether, di-isopropyl ether, dibutyl ether, propylene oxide, dioxane and tetrahydrofuran; ketones, for example, acetone, methyl ethyl ketone, methyl isopropyl ketone and methyl isobutyl ketone; nitriles, such as acetonitrile, propionitrile and acrylonitrile; and esters such as ethyl acetate, amyl acetate and the like.

The reaction temperature of the process (a) may be varied within a wide range. In general, the process (a) may be carried out at a temperature of about 0° to 100° C., preferably at a temperature of about 50° to 80° C. The reaction is preferably allowed to take place under normal pressure, although it is also possible to conduct the reaction under a higher or lower pressure.

To carry out the process (a), about 1 to 1.5 moles, preferably about 1 to 1.2 moles of trichloromethyl chloroformate may be employed per mole of the starting compound (II). This reaction may be conducted in an inert solvent, for instance, ethyl acetate.

In carrying out the process (b), use may be made of an inert solvent as employed in the process (a), although it is also possible to use other solvents such as alcohols, acid amides, sulfones, sulfoxides and the like.

The reaction temperature of the process (b) may be varied within a wide range. The reaction may generally be carried out at a temperature of about 0° to 60° C., preferably about 20° to 40° C. Although the reaction is preferably conducted under normal pressure, it is also possible to carry out the reaction under a higher or lower pressure.

In carrying out the process (b), carbon disulfide may be used in an amount of about 1 to 1.5 moles, preferably about 1 to 1.2 moles per mole of the starting compound (II). The reaction may be conducted in the presence of an inert solvent, e.g. ethanol, and also in the presence of sodium hydroxide.

To carry out the process (c), use may be made of an inert solvent as employed in the process (a).

The reaction temperature of the process (c) may be varied within a wide range. In general, the reaction may be carried out at a temperature of about −70° to +150° C., preferably at a temperature of about −70° to +100° C. It is advantageous to conduct the reaction under normal pressure, although it is also possible to employ a higher or lower pressure.

In carrying out the process (c), carbonyl sulfide may be used in an amount of about 1 to 1.5 moles, preferably about 1 to 1.2 moles per mole of the starting compound (II). The reaction may be conducted in the presence of an inert solvent, e.g. ethanol, and also in the presence of sodium hydroxide.

In carrying out the process (d), use may be made of an inert solvent as employed in the process (b).

The reaction temperature of the process (d) may be varied within a wide range. The reaction may generally be carried out at a temperature of about 0° to 40° C., preferably about 0° to 20° C.

Although the reaction is preferably conducted under normal pressure, it is also possible to conduct the reaction under a higher or lower pressure.

In carrying out the process (d), nitric acid may generally be employed in an amount of about 1 to 1.5 moles, preferably about 1 to 1.2 moles per mole of the starting compound (II). The reaction may be carried out in an inert solvent, e.g. a mixture of glacial acetic acid and acetic acid anhydride.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonoadaceae, Rhizobiaceae, Enterobacteriaceae, Corynebacteriaceae and Streptomycetaceae.

Some causative organisms of fungal and bacterial diseases included under the abovementioned main headings, are mentioned below as non-limiting examples:

Xanthomonas specie, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as for example, *Pythium ultimum;*
Phytophthora species, such as, for example, *Phytophthora infestans;*
Pseudoperonospora species, such as, for example, *Pseudoperonospora cubensis;*
Plasmopara species, such as, for example, *Plasmopara viticola;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graninea*
(Conidial form: Drechslera, Synonym: Helminthosporium);
Cochliobolus species, such as, for example, *Cochliobolus sativus*
(Conidial form: Drechslera, Synonym: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted into the customary formulations, such as solutions, emulsions, suspensions, powders, foams, pastes, granules, aerosols, natural and synthetic materials impregnated with active compound, very fine capsules in polymer substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chlorine, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules or organic materials such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phosphopholipids, such as cephalins and lecithins, and synthetic phospholipids, can be used in the formulation. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron manganese boron, copper, cobalt, molybdenum and zinc.

The formulation in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, of 0.00001 to 0.1% by weight, especially of 0.0001 to 0.02%, are generally employed.

The present invention is further illustrated by way of examples. However, it should be noted that the scope of the invention is not limited only to that of the examples.

PREPARATIVE EXAMPLES

EXAMPLE 1

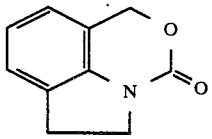

(Compound No. 1)

10 ml of trichloromethyl chloroformate are dissolved in 80 ml of ethyl acetate. To the resulting solution, a solution of 4.00 g of 7-hydroxymethyl-2,3-dihydroindole in 20 ml of ethyl acetate is added.

The reaction solution is heated under reflux for 3 hours. The reaction solution is cooled to room temperature, and the solvent is distilled off under a reduced pressure. The residue is recrystallized in ethanol to obtain 3.34 g of 4,5-dimethylene-2,4-benzoxazin-3-one having a melting point of 138° to 139° C.

In analogous manner, the following compounds were prepared:

Compound No. 2: 4,5-trimethylene-2,4-benzoxazine-3-one
$^1$H-NMR (CDCl$_3$, δppm)
1.99 (2H, m), 2.77 (2H, t)
3.83 (2H, t), 5.17 (2H, s)
6.83–7.27 (3H, m)

Compound No. 3: 6-chloro-4,5-trimethylene-2,4-benzoxazin-3-one
$^1$H-NMR (CDCl$_3$, δppm)
2.00 (2H, m), 2.83 (2H, t)
3.73 (2H, t), 5.07 (2H, s)
6.80 (1H, d), 6.97 (1H, d)
mp. 98°–103° C.

Compound No. 4: 7-methyl-4,5-trimethylene-2,4-benzoxazine-3-one
$^1$H-NMR (CDCl$_3$, δppm)
2.07 (2H, m), 2.30 (3H, s)
2.73 (2H, t), 3.80 (2H, t)
5.13 (2H, s), 6.70 (1H, bs)
6.83 (1H, bs)
mp. 117°–120° C.

Compound No. 5: 7-chloro-4,5-trimethylene-2,4-benzoxazin-3-one
$^1$H-NMR (CDCl$_3$, δppm)
2.00 (2H, m), 2.70 (2H, t)
3.83 (2H, t), 5.10 (2H, s)
6.80–7.07 (2H, m)
mp. 106°–111° C.

EXAMPLE 2

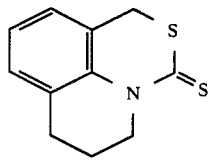

(Compound No. 6)

1.60 g of 8-hydroxymethyl-1,2,3,4-tetrahydroquinoline and 1.0 g of sodium hydroxide are dissolved in 20 ml of ethanol and 2 ml of carbon disulfide are added thereto. The reaction solution is heated under reflux for 12 hours. The reaction mixture is cooled to room temperature. The crude product, which has been precipitated, is separated by means of filtration, and then washed in ether.

1.76 g of 4,5-trimethylene-2,4-benzothioxazine-3-thione are obtained as light yellowish crystals.

$^1$H-NMR (CDCl$_3$, δppm)
2.03 (2H, m), 4.47 (2H, t)
2.83 (2H, t), 6.70–7.20 (3H, m)
3.73 (2H, s)

In manner analogous to Example 2, the following compounds were produced:

Compound No. 7: 4,5-dimethylene-2,4-benzothioxazine-3-thione
mp. 153° to 155° C.

Compound No. 8: 6-chloro-4,5-trimethylene-2,4-benzothioxazine-3-thione
mp. 187° to 194° C.

Compound No. 9: 7-methyl-4,5-trimethylene-2,4-benzothioxazine-3-thione
mp. >300° C.

EXAMPLE 3

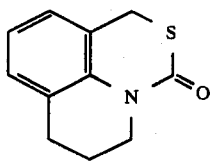

(Compound No. 10)

2.60 g of 8-hydroxymethyl-1,2,3,4-tetrahydroquinoline and 2.0 g of sodium hydroxide are dissolved in 30 ml of ethanol. The resulting solution is cooled to a temperature of −70° C. Thereafter, gaseous carbonyl sulfide is introduced into the reaction mixture at −70° C. for 1 hour, so that about 3 g of carbonyl sulfide is reacted. The reaction mixture is agitated for 4 hours so that the reaction mixture is slowly warmed to room temperature. Thereafter, the reaction mixture is heated under reflux for 3 hours.

The reaction mixture is then poured into 100 ml of water, and an extraction operation is effected with the aid of ethyl acetate. Then the mixture is dried over sodium sulfate. The solvent is distilled off to obtain a yellow oil, which is then subjected to chromatography employing a silica gel column (carbon tetrachloride/chloroform=1). 4,5-Trimethylene-2,4-benzothioxazin-3-one is obtained as yellow oil in an amount of 0.43 g.

$^1$H-NMR (CDCl$_3$, δppm)
1.93 (2H, m), 3.53 (2H, s)
2.80 (2H, t), 6.37–7.10 (3H, m)
3.30 (2H, t).

EXAMPLE 4

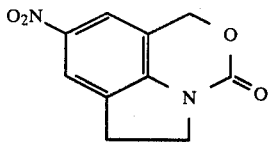

(Compound No. 11)

1.00 g of 4,5-dimethylene-2,4-benzoxazine-3-one is dissolved in a mixture of 10 ml of glacial acetic acid and 1.14 g of acetic acid anhydride. To the resulting solution, 0.4 ml of concentrated nitric acid is added under stirring at 10° C.

The reaction solution is slowly warmed up to room temperature, and the reaction solution is stirred for further 3 hours. Thereafter, the reaction solution is poured into 50 ml of water, and extracted with ether. The organic layer is washed in water, and dried over sodium sulfate.

After the solvent has been distilled off, 0.47 g of 7-nitro-4,5-dimethylene-2,4-benzoxazin-3-one is obtained, m.p. 238° to 242° C. (decomposition).

EXAMPLE 5

(Preparation of intermediate compound)

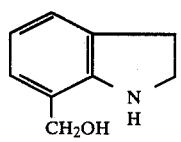

1.3 g of lithium aluminum hydride are suspended in 10 ml of anhydrous ether under a nitrogen atmosphere. The resulting suspension is cooled to a temperature of −20° C., and admixed with a solution of 2.00 g of 2,3-dihydroindole-7-carboxylic acid methyl ester in 20 ml of anhydrous ether. The reaction solution is stirred at the above-mentioned low temperature of −20° C. for 1 hour. After that, a small amount of water is added to the reaction solution to hydrolyze or decompose the excess of lithium aluminum hydride.

After the reaction solution has been allowed to warm to room temperature, the reaction solution is filtered through a Celite filter. The solvent is distilled off from the filtrate, so that 1.5 g of 7-hydroxymethyl-2,3-dihydroindole are obtained.

$^1$H-NMR (CDCl$_3$, δppm)
2.93 (2H, t) 6.45–6.93 (3H, m)
3.43 (2H, t)
4.43 (2H, t)

In manner analogous to Example 5 the following compound was prepared:
5-chloro-8-hydroxymethyl-1,2,3,4-tetrahydroxy-quinoline $^1$H-NMR (CDCl$_3$, δppm)
1.93 (2H, m) 4.46 (2H, s)
2.70 (2H, t) 4.60–5.10 (2H, m)
3.23 (2H, t) 6.47 (1H, d)
6.67 (1H, d)

EXAMPLE 6

(Preparation of starting material)

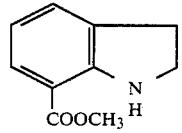

1.75 g of indole-7-carboxylic acid methyl ester and 2.92 g of borane-trimethylamine complex are dissolved in 10 ml of dioxane. To the resulting solution, 2 ml of concentrated hydrochloric acid are added. The reaction solution is heated under reflux for 30 minutes, and then cooled to room temperature. 10 ml of 6N hydrochloric acid are added to the reaction solution, which is then refluxed under heating for 15 minutes, and thereafter cooled to room temperature. The reaction solution is poured into 50 ml of water. The resulting mixture is neutralized with a 2N aqueous sodium hydroxide solution, and then extractd with ether. The organic layer is washed with a saturated aqueous sodium chloride solution, and dried over anhydrous sodium sulfate. After the solvent has been distilled off, 1.26 g of 2,3-dihydroindole-7-carboxylic acid methyl ester are obtained, mp. 70° to 73° C.

BIOTEST EXAMPLES

Comparative active compound A-1(known from Japanese Patent Application Disclosure No. 62829-1978)

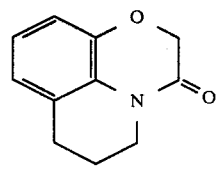

Comparative active compound B-1 (known from Japanese Patent Application Disclosure No. 132232-1979)

USE EXAMPLES

Blast test/rice plant/application of active compounds to stems and leaves of plant Formulation of active compound Active compound: 50 parts by weight
Carrier: 45 parts by weight of mixture of diatomaceous earth and kaolin (1:5)
Emulsifier: 5 parts by weight of polyoxyethylenealkylphenylether The stated amount of active compound was milled and mixed with the stated amount of carrier and the stated amount of emulsifier to obtain a concentrated emulsifiable composition which was then diluted with water.

Biotest Example A

Test method

Rice plants (Kusabue Variety) were grown in vinyl plastic pots with a diameter of 7.5 cm. When the plants were grown to a 3- or 4-leaved stage, they were sprayed with a spray solution containing the active compound in the predetermined concentration. The amount of the spray solution was 50 ml per three pots.

On the next day, the plants were inoculated by means of a spraying operation with an aqueous spore suspension of rice blast, and incubated in a humidity chamber at 25° C. under 100% relative atmospheric humidity.

Seven days after the inoculation, the degree of infection of the rice plants was determined with the aid of the scale shown below.

| Degree of infection | Infected area (%) per total area of observed portion of plant |
| --- | --- |
| 0 | 0 |
| 0.5 | 2 or less |
| 1 | 3–5 |
| 2 | 6–10 |
| 3 | 11–20 |
| 4 | 21–40 |
| 5 | 41 or more |

The degree of plant protection (%) was calculated according to the mathematical formula shown below:

$$\text{Degree of protection (\%)} = \left(\frac{X - Y}{X}\right) \times 100$$

wherein
X = Degree of infection is untreated plants (control);
Y = Degree of infection in treated plants In this test, one treatment consisted of three pots. The test results are shown in Table A.

TABLE A

| | Amount of active compound (ppm) | Degree of protection (%) |
| --- | --- | --- |
| Active compound | | |
| No. 1 | 100 | 100 |
| No. 2 | 100 | 100 |
| No. 3 | 100 | 100 |
| No. 4 | 100 | 100 |
| No. 6 | 100 | 100 |
| Comparative compound | | |
| A-1 | 100 | 80 |
| B-1 | 100 | 74 |

Biotest Example B

Blast test/rice plant grown in paddy field/application of active compound to water surface of paddy field.

Test method

3 Rice plants (Kusabue Variety) per pot were grown in white porcelain pots with irrigation.

When the rice plants were grown to the early tiller stage or the young ear formation stage, a predetermined amount of a fungicidal solution was poured into the water on the surface of pots.

The fungicidal solutions, were prepared in the same manner as in Biotest Example A, and contained the active compound in a predetermined concentration.

After 21 days, the rice plants were inoculated in conventional manner by spraying with an aqueous spore suspension of rice blast. The plants were then placed in a room at 25° C. under a relative atmospheric humidity of 100% for 24 hours.

Thereafter the plants were kept in a greenhouse at a temperature of 20°–28° C.

Seven days after the inoculation, the rice plants were observed, and the degree of protection (%) was calculated as in Biotest Example A.

The test results are shown in Table B.

TABLE B

| | Amount of active compound (mg/m$^2$) | Degree of protection (%) |
| --- | --- | --- |
| Active compound | | |
| No. 1 | 200 | 100 |
| No. 2 | 200 | 100 |
| No. 3 | 200 | 100 |
| No. 4 | 200 | 100 |
| Comparative compound | | |
| A-1 | 200 | 60 |
| B-1 | 200 | 47 |

It is understood that the specification and examples are illustrative but not limitative of the present invention and that other embodiments within the spirit and scope of the invention will suggest themselves to those skilled in the art.

We claim:

1. A cyclic carbamate of the formula

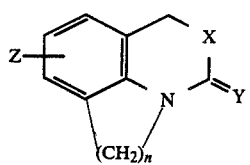

in which

X and Y each represent oxygen or sulfur,

Z represents hydrogen, halogen, alkyl or nitro, and n is 2 or 3.

2. A compound according to claim 1, in which

X and Y represent oxygen,

Z represents hydrogen, fluorine, chlorine, bromine, nitro, or alkyl with 1 to 4 carbon atoms, and n is 2 or 3.

3. A compound according to claim 1, in which

X and Y each represent oxygen,

Z represents hydrogen, fluorine, chlorine, bromine, methyl or ethyl, and n is 2.

4. A compound according to claim 1, wherein such compound is 4,5-dimethylene-2,4-benzoxazin-3-one of the formula

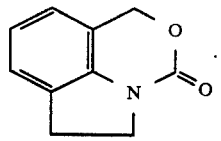

5. A compound according to claim 1, wherein such compound is 4,5-trimethylene-2,4-benzoxazin-3-one of the formula

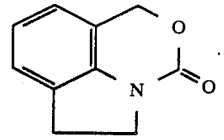

6. A compound according to claim 1, wherein such compound is 6-chloro-4,5-trimethylene-2,4-benzoxazin-3-one of the formula

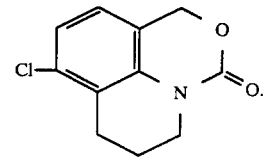

7. A compound according to claim 1, wherein such compound is 7-methyl-4,5-trimethylene-2,4-benzoxazine-3-one of the formula

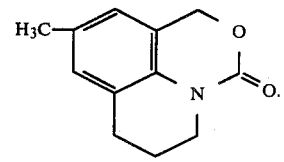

8. A fungicidal composition comprising a fungicidally effective amount of a compound according to claim 1 and a diluent.

9. A method of combating fungi which comprises applying to such fungi or to a fungus habitat a fungicidally effective amount of a compound according to claim 1.

10. The method according to claim 9, wherein such compound is 4,5-dimethylene-2,4-benzoxazin-3-one,
4,5-trimethylene-2,4-benzoxazin-3-one,
6-chloro-4,5-trimethylene-2-benzoxazin-3-one or
7-methyl-4,5-trimethylene-2,4-benzoxazin-3-one.

* * * * *

UNITED STATES PATENT AND TRADEMARK OFFICE
CERTIFICATE OF CORRECTION

PATENT NO. : 4,729,998
DATED : March 8, 1988
INVENTOR(S) : Kurahashi et al.

It is certified that error appears in the above-identified patent and that said Letters Patent is hereby corrected as shown below:

| | |
|---|---|
| Title Page, under "Abstract", bottom of formula | Delete "$(CH_2)n$" and substitute -- 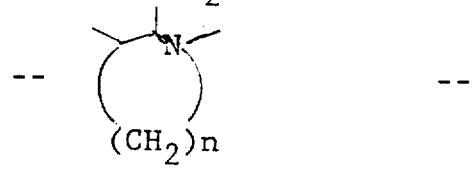 -- |
| Col. 11, line 67 | Delete "is" and substitute --in-- |
| Col. 14, bottom of 1st formula | Delete " 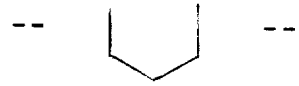 " and substitute |

-- ⌊⌡ --

Signed and Sealed this

Thirteenth Day of September, 1988

Attest:

DONALD J. QUIGG

*Attesting Officer*  *Commissioner of Patents and Trademarks*